United States Patent [19]

Melby

[11] 4,051,079

[45] Sept. 27, 1977

[54] REGENERATION OF ACIDIC CATION EXCHANGE RESIN USING ACIDIFIED PHENOL-WATER MIXTURE

[75] Inventor: Earl George Melby, Somerville, N.J.

[73] Assignee: Union Carbide Corporation, New York, N.Y.

[21] Appl. No.: 698,764

[22] Filed: June 22, 1976

[51] Int. Cl.$^2$ .......................... B01D 15/06; B01J 1/09
[52] U.S. Cl. ............................... 260/2.2 R; 210/30 R
[58] Field of Search ........................... 210/32, 30 R; 260/2.2 R; 526/495

[56] References Cited

PUBLICATIONS

Kurin, "Ion Exchange Resin", Krieger (Poblstr) Huntington, N. Y. 1972, pp. 34-47.

Primary Examiner—Joseph L. Schofer
Assistant Examiner—Peter F. Kulkosky
Attorney, Agent, or Firm—Franklyn Schoenberg

[57] ABSTRACT

Acidic cation exchange resin whose activity has been reduced by fouling from phenolic tars and/or by contamination by metal ions, is regenerated by treating such resin with an acidified phenol/water wash.

8 Claims, 1 Drawing Figure

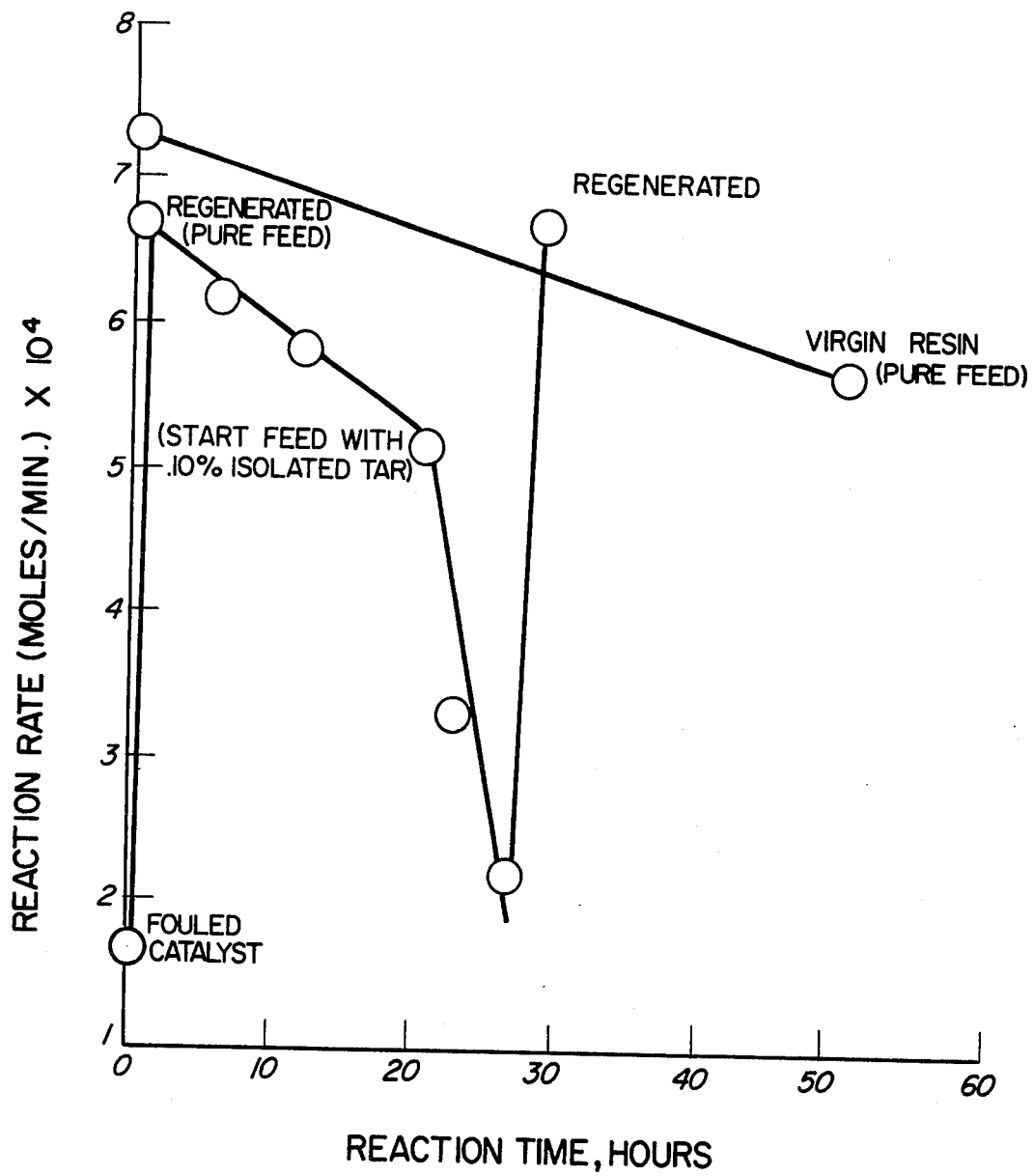

REGENERATION OF ACIDIC CATION EXCHANGE RESIN USING ACIDIFIED PHENOL-WATER MIXTURE

The invention relates to a method for regenerating acidic cation exchange resins that have been fouled by phenolic tars and/or by contamination by metallic ions.

BACKGROUND OF THE INVENTION

Acidic cation exchange resin is an important catalyst in reaction processes utilizing phenols and/or substituted phenols. The most commercially important of such processes today is the reaction of phenol with acetone to form bisphenol-A. For instance, see Farnham et al., U.S. Pat. No. 3,242,219.

The acidic cation exchange resins utilized in such processes gradually lose activity. As a result, after a period of time, perhaps 1 or 2 years, the catalyst must either be replaced or regenerated. Two important causes of such loss of activity, either of which can occur, are:

1. Contamination by metal ions, which neutralize the active acid sites; and
2. Fouling with organic tars, which blocks access by the reactants to the active catalyst sites.

The present invention provides a method for regenerating acidic cation exchange resin that has been deactivated by contamination with metallic ions, and/or which has been fouled by phenol-derived organic tars. The method is particularly useful or bisphenol-A process catalyst, but is also useful for regenerating acidic cation exchange resin from other processes wherein the deactivation is caused by fouling with phenol-derived organic tars, and/or by contamination by metallic ions.

SUMMARY OF THE INVENTION

The process of the invention comprises contacting (a) an acidic cation exchange resin that has been deactivated by fouling with phenol-derived organic tars and/or by contamination with metallic ions, with (b) a phenol/water mixture that contains an acid having a pKa of less than about 3.

PRIOR ART

A leading manufacturer of acidic cation exchange resin has disclosed, in a Technical Bulletin, that fouled resin can be reactivated to at least 90 percent of its original catalytic activity by contacting the fouled resin at 90° to 100° C. for 4 to 8 hours with 98 percent sulfuric acid. The difficulty (e.g., corrosion problems) inherent in using such a treatment on a commercial scale is obvious.

Kutsenko et al., in Soviet Plastics, No. 8, 27 (1970), disclosed reactivating fouled bisphenol process acidic cation exchange resin by treating with acetone, alcohol, toluene, a phenol-toluene mixture, or phenol. "Best results were obtained when the catalyst was washed with a phenol melt at 40°-50° C. This wash completely removes the PA bisphenol [the reaction product of phenol and diallylidenepentaerythritol] and the resinous substances absorbed and re-establishes the operating conditions of the column without reducing the activity of the catalyst. The wash lasts for 30–40 minutes." The authors also refer to another article that discloses regenerating acidic cation exchange resin by treating with benzene, followed by successive wahses with 95 percent sulfuric acid and water.

In U.S. Pat. No. 3,887,498 (issued June 3, 1975), Kuhajek et al. disclose a process for regenerating and removing iron from a cation exchange resin which has become exhausted and iron-fouled as the result of use in softening water, by treating with an aqueous solution of sodium chloride and nitrilotriacetic acid.

Huang et al., in U.S. Pat. No. 3,855,343 (issued Dec. 17, 1974), disclose the regeneration of acidic cation exchange resin that is complexed with boron trifluoride, and which is used in an isoparaffin/olefin alkylation, with polar solvents, particularly $C_1$-$C_5$ alcohols, or water.

DESCRIPTION OF THE INVENTION

The acidic cation exchange resins that are employed in the invention are a known and commercially available class of compositions. Typically, they are the sulfonated reaction products of styrene/divinylbenzene copolymers. The invention can be employed with both the microreticular or gel type, and the macroreticular type, of acidic cation exchange resins.

A major aspect of the invention is in regenerating acidic cation exchange resins that have been fouled by phenol-derived organic tars. The term "phenol-derived organic tars" refers to those phenol derived compositions, including alkylated phenols, bisphenols, higher polyphenols, and the like, that are present in a process stream of a reaction process utilizing a phenol as one of the reactants. In a bisphenol-A process stream, such tars would include isopropenylphenol, isopropenylphenol dimers and oligomers, Dianin's compound, spiroindane bisphenol, and a complex mixture of other compositions including trisphenols and higher polyphenols. Other processes utilizing a phenol as a reactant such as other phenol/carbonyl compound condensation processes, would form other types of phenols, bisphenols, trisphenols, and higher polyphenols as by-product tars.

The invention is also useful in removing metallic ion contamination of acidic cation exchange resin. Such contamination often occurs to a minor degree in conjunction with fouling with tars, as described above. However, it can be the principal cause of loss of activity, in some cases.

The catalyst regenerating composition is a phenol-water solution containing an acid having a pKa of less than about 3, and preferably less than about 2. The reason that a phenol/water mixture is much more effective in this process than phenol alone, is not known for certain. However, it is probable that the increased ionization of the acid in the presence of water is a significant factor, and further, the phenol/water mixture may be a better solvent for some of the constituents of the tars than is phenol alone. The proportions of phenol and water have not been found to be narrowly critical but operation of the invention should be within the following broad guidelines:

Phenol should be the major component of the phenol/water mixture. The minimum amount of water at which the advantages of the invention begin to be observed is a few percent (e.g., about 2 to 3 weight percent), based on weight of phenol plus water. The maximum amount of water will be that point at which the mixture is no longer a good solvent for the tars. This can be determined routinely on a case-by-case basis. A convenient maximum is about 30 weight percent water, based on weight of phenol plus water, because at higher proportions of water, the mixture is no longer one phase at room temperature. The preferred proportions are from about 5 to about 10 weight percent water, based on weight of phenol plus water.

Any acid having a pKa of less than about 3 can be used in the invention. Examples include paratoluenesulfonic acid, benzenesulfonic acid, sulfuric acid, hydrochloric acid, trifluoroacetic acid, citric acid, and trichloroacetic acid. Organic acids are preferred, and the sulfonic acids are more preferred.

The proportion of acid in the phenol/water mixture is not at all critical. It is preferred to use the acid in at least a certain minimum total amount, termed "a minimum effective amount". The exact minimum effective amount can be determined on a case-by-case basis by routine experiments. For Acidic Cation Exchange Resin A, described below in the experimental section, it has been found that the minimum effective amount of para-toluenesulfonic acid is about 1 gram of acid per 10 to 20 grams of dry catalyst. (The minimum effective amount varies not only from one ion exchange resin to another, but also with different samples of the same resin, depending on the condition of the resin.) The minimum effective amount of acid has been employed in the process of the invention when the use of more acid fails to result in a significant increase in the acidity of the treated resin.

The process of this invention is carried out by passing the acidified phenol/water mixture through a bed of the deactivated acidic cation exchange resin. The total volume of phenol/water mixture employed is not at all critical. A minimum of about 1 to 1½ times the total resin bed volume is usually needed. More can be used, if desired. Resin beds having lower length to diameter ratios will usually require more total phenol/water mixture than a bed having the same volume, but a higher length to diameter ratio.

The temperature of the phenol/water mixture is not critical. Any temperature above the freezing point of the phenol/water mixture, and below the boiling point of water, can be used. At temperatures above about 120° C., the sulfonic acid groups of the acidic cation exchange resin become unstable. Therefore, such temperatures are preferably avoided.

The rate at which the phenol/water mixture is passed through the resin bed has not been found to be critical. The Examples, below, illustrate throughput rates that are convenient in laboratory scale equipment. Greater or lesser throughput rates can be employed, if desired.

A preliminary phenol wash of the resin bed can be used, if desired. This will remove some tars, and will reduce the total amount of acidified phenol/water mixture required. A final phenol wash is desirable to dry the resin and to remove the free acid.

In the experiments below, the quantities of phenol and water used are often stated in volume (milliliters) rather than weight. Because the specific gravities of phenol and water are so close, the weight and volume proportions of these two materials are substantially the same. Unless otherwise indicated, the weights given for the ion exchange resins are wet weights (i.e., the resins are wet with a mixture that is predominantly phenol). The dry resin weight is about one-half the wet weight.

GENERALIZED EXPERIMENTAL PROCEDURE

A. Regeneration Method

A typical regeneration experiment can be described as follows: Used acidic cation exchange resin (35 grams wet weight) was taken as received and placed in a column (2.5 centimeter diameter). The column is heated to 50° C. with heating tapes. Phenol (200 milliliters) is slowly passed downflow by gravity through the resin (1 drop/second). The phenol wash is followed with a wash consisting of 180 milliliters of phenol, 20 milliliters of water, and 3.35 grams of p-toluenesulfonic acid monohydrate. A final wash consists of 200 milliliters of dry phenol. The resin is then removed from the column for activity determinations. All other variations of the procedure were similarly performed.

B. Determination of Acidity in Ion Exchange Resins

The accuracy obtained from ion exchange resin titrations is very dependent on the drying conditions. As described in the literature, * if the resins are dried slowly, the monohydrates of the acid substituents are formed. Once the monohydrate is formed, the water molecule cannot be removed even by very strong drying (150° C.). The strong attachment of the water molecule is caused by three or four hydrogen bonds. If the resin is dried rapidly, the higher (di and tetra) hydrates break down and immediately desorb before the monohydrate becomes attached.

G. Zundel, "Hydration and Intermolecular Interaction," Academic Press, Inc., 1969, New York, New York, p. 158.

This monohydrate structure changes the weight of the ion exchange resin and results in error (lower values) for the acidity as determined by titration. In order to circumvent these difficulties, the drying method reported by Gates* is used. Thus, 2 grams of wet resin are placed in a small vial. The vials are placed in a 110° C. vacuum oven at full vacuum overnight. The vials are immediately capped when hot and the weight of the resin is obtained. The resin is transferred into a 250-milliliter Erlenmeyer flask, and 125 milliliters of water and 5 grams of NaCl is added. The mixtures are swirled for 30 minutes and titrated at a phenolphthalein end point with 0.100N NaOH.

*B.C. Gates et al., Journal of Catalysis, 14, 69–76 (1969)

C. Determination of Catalytic Activity by Batch Reactions

The catalytic activity of used and regenerated ion exchange resins were determined in laboratory batch reactions using standard methods, such as that described below in Example 1.

D. Analysis of Batch Reaction Samples 1 gram samples were removed from the batch reactions after 15 minutes and immediately cooled. In order to allow the quick analysis of very large numbers of samples; the % bisphenol-A was determined using nmr (nuclear magnetic resonance) by relating the product methyl peak to a weighed amount of internal standard (dioxane). Although this method does not provide the precision of the accepted gas chromatographic analysis, it serves as a quick and reliable way to screen large differences in catalytic activity. Initial experiments run in duplicate demonstrated that the method is reproducible. It is most reliable when ethyl mercaptan is used as a promoter, which results in samples containing small amounts of the 2,4'-isomer and other impurities.

E. Continuous Studies

Continuous studies were carried out using the following technique: 11 Grams of dry catalyst were placed in a 0.5 inch diameter stainless steel tube. Reactants were fed through the catalyst from a heated reservoir using a micropump. The reactor was immersed in a 70°±1° C. bath. Typical feed was composed of 376.44 grams of dry phenol, 23.24 grams of acetone and 0.96 milliliter of ethanethiol. Samples were collected at various time intervals, and the rate of reaction was determined by measuring the percent water by Karl Fischer analysis.

In the Examples, the following acidic cation exchange resins were employed:

Ion Exchange Resin A—A macroreticular resin comprising the sulfonated product of a styrene/divinylbenzene copolymer (containing about 20 mole percent divinylbenzene), and having a surface area of about 45 square meters per gram of dry resin.

Ion Exchange Resin B—Similar to Ion Exchange Resin A, except for having a surface area of about 600 square meters per gram of dry resin.

Ion Exchange Resin C—A microreticular of gel-type resin comprising the sulfonated product of a styrene/-divinylbenzene copolymer containing about 4 mole percent divinylbenzene.

EXAMPLE 1

A 2.5 centimeter diameter column was charged with 35 grams wet weight (10.7 cubic centimers) of used Ion Exchange Resin A from a bisphenol-A process. Phenol, 200 milliliters, was slowly passed (3 milliliters/minute) through the resin bed by gravity at 60° C. to remove surface contamination consisting of bisphenol-A and related by-products. The effluent was initially black and later became colorless. A regeneration mixture was prepared consisting of 1.67 grams of p-toluenesulfonic acid monohydrate, dissolved in 180 milliliters of phenol and 20 milliliters of water. This mixture was slowly passed by gravity (at a rate of about 3 milliliters/minute) through the resin bed. At first, the effluent was very black but gradually became colorless. The regeneration step was followed with a wash with pure phenol (100 milliliters). The regenerated resin was removed from the column, washed with methanol, and dried with full vacuum for 24 hours. The acidity was determined by direct titration with 0.100N NaOH. The catalyst reactivity was determined by carrying out batch reactions, as follows:

A 125-milliliter Erlenmeyer flask with stirrer was charged at 70° C. with 10 grams of dry regenerated resin, 48 grams of distilled phenol, 2.78 grams of reagent grade acetone, and 0.12 milliliter of ethanethiol. After 15 minutes, a 10-milliliter aliquot was withdrawn and the percent conversion was determined by nmr. Table I compares the results obtained for inactive (i.e., used), regenerated, and virgin resins. The regenerated resin has an acidity of 4.30 millequivalents/gram and a catalytic activity equivalent to virgin Ion Exchange Resin A. Furthermore, there was a significant improvement of the color of the reaction mixture product after regeneration. No additional adsorbed tar can be extracted from the regenerated catalyst by any other known method, which fact emphasizes the effectiveness of this procedure.

In Table I, and elsewhere in the examples, the term "PTSA regenerated", or just "PTSA" alone, refers to the treatment with para-toluenesulfonic acid in phenol/water solution.

TABLE I

| Ion Exchange Resin A | Treatment | Acidity, millequivalents/gram | Reactivity* % Bis-A- 15 minutes | Product Reaction Mixture Color |
|---|---|---|---|---|
| Virgin | phenol wash | 4.78 | 71.4 | White |
| Used | phenol/$H_2O$ (90/10) | 3.60 | 17.4 | Brown |
| Used | $CH_3OH$ wash | 3.62 | 20.0 | Brown |
| Used | PTSA regenerated | 4.28 | 75.0 | White |

*Per cent conversion of reactants to bisphenol-A, the per cent being based on total amount of acetone in the starting reaction mixture.

EXAMPLE 2

Using the generalized experimental procedure, a number of Ion Exchange Resin A catalyst samples from commercial bisphenol-A processes were regenerated in accordance with the invention. The results are displayed in Table II. Sample No. 7 was virgin resin.

TABLe II

| Sample No. | Catalyst Age, Months | Treatment | Acidity, (millequivalents/gram) | Reactivity, % Conversion to Bisphenol-A |
|---|---|---|---|---|
| 1 | 24 | $CH_3OH$ | 3.78 | 10%/15 minutes |
|   | 24 | PTSA | 4.23 | 81%/15 minutes |
| 2 | 24 | $CH_3OH$ | 3.33 | 20%/15 minutes |
|   | 24 | PTSA | 3.83 | 59%/15 minutes |
| 3 | 28 | $CH_3OH$ | 3.50 | 3%/15 minutes |
|   | 28 | Phenol/$H_2O$ | 3.60 | 17%/15 minutes |
|   | 28 | PTSA | 4.28 | 75%/15 minutes |
| 4 | 13 | $CH_3OH$ | 3.20 | 0%/20 minutes |
|   | 13 | PTSA | 4.22 | 68%/15 minutes |
| 5 | 4 | $CH_3OH$ | 3.62 | 20%/15 minutes |
|   | 4 | PTSA | 4.59 | 70%/15 minutes |
| 6 | 6 | $CH_3OH$ | 3.49 | 1.67%/20 minutes |
|   | 6 | PTSA | 4.64 | 86%/15 minutes |
| 7 | — | Phenol Wash | 4.78 | 71%/15 minutes |

EXAMPLE 3

Using the generalized experimental procedure, with variations as indicated, a series of used Ion Exchange Resin A catalyst samples (from a bisphenol-A process) were treated as indicated in Table III, below. In the Table, "Column L/D" refers to the length to diameter ratio of the catalyst treating bed. In Runs 1-12, the same used catalyst was employed. Prior to treatment, its acidity was 3.50 millequivalents/gram and its reactivity (% conversion to bisphenol-A in a batch reaction at 70° C. for 15 minutes) was 3 percent. Runs 13 and 14 employed a different used catalyst whose acidity and reactivity prior to treatment were 3.78 millequivalents/gram and 10 percent conversion. Runs 15 and 16 used a third catalyst whose acidity and reactivity prior to treatment were 3.08 millequivalents/gram and 20 percent conversion. In runs 11, 14, and 16, the regeneration solution was recycled through the catalyst. In Run No. 12, no prior phenol wash was used.

TABLE III
THE EFFECT OF VARIABLES ON THE PHENOL/$H_2O$/PTSA REGENERATION PROCEDURE

| Run No. | Gms. Catalyst | Ml.Phenol | Ml.$H_2O$ | Gms. PTSA | Column L/D | Acidity, Meq/gm. | Conversion (15 min.) |
|---|---|---|---|---|---|---|---|
| 1 | 35 | 180 | 20 | 3.35 | 4.28 | 4.28 | 68 |
| 2 | 35 | 190 | 10 | 3.35 | 4.28 | 4.23 | 66 |
| 3 | 35 | 200 | — | 3.35 | 4.28 | 3.96 | 56 |

TABLE III-continued
THE EFFECT OF VARIABLES ON THE PHENOL/H$_2$O/PTSA REGENERATION PROCEDURE

| Run No. | Gms. Catalyst | Ml.Phenol | Ml.H$_2$O | Gms. PTSA | Column L/D | Acidity, Meq/gm. | Conversion (15 min.) |
|---|---|---|---|---|---|---|---|
| 4 | 35 | 180 | 20 | 6.70 | 4.28 | 4.28 | 70 |
| 5 | 35 | 180 | 20 | 3.35 | 4.28 | 4.28 | 68 |
| 6 | 35 | 180 | 20 | 1.67 | 4.28 | 4.26 | 75 |
| 7 | 35 | 180 | 20 | 0.83 | 4.28 | 4.04 | 52 |
| 8 | 80 | 410 | 46 | 7.66 | 0.706 | 4.24 | 62 |
| 9 | 80 | 135 | 15 | 7.66 | 0.706 | 4.29 | 72 |
| 10 | 80 | 135 | 15 | 3.35 | 0.706 | 4.27 | 64 |
| 11 | 80 | 135 | 15 | 6.70 | 0.706 | 4.04 | 59 |
| 12 | 80 | 135 | 15 | 7.66 | 0.706 | 4.30 | 78 |
| 13 | 80 | 135 | 15 | 7.66 | 0.706 | 4.35 | 74 |
| 14 | 80 | 135 | 15 | 7.66 | 0.706 | 3.76 | 45 |
| 15 | 80 | 135 | 15 | 7.66 | 0.706 | 3.76 | 45 |
| 16 | 80 | 135 | 15 | 7.66 | 0.706 | 3.78 | 53 |

EXAMPLE 4

Regeneration Studies in a Continuous Reactor

Inactive Ion Exchange Resin A (the same catalyst as Sample No. 4 in Table II) was charged to a small continuous reactor, and the rate of formation of bisphenol-A was measured by determining the percent water generated by Karl Fischer analysis. This particular catalyst was chosen since it was judged to be in the worst condition. Regeneration by the PTSA method was carried out directly in the reactor. The results are illustrated in FIG. 1. After regeneration, the rate of reaction using pure reactants was measured over 20 hours. The catalyst was then intentionally fouled using a feed containing tar isolated from fouled resin. Regeneration again restored the catalytic activity of the resin. These results point out the dramatic increase in reaction rate after regeneration and demonstrate the feasibility of successive regenerations.

EXAMPLE 5

Regeneration Using Other Acids and Solvents

Other acids (of varying pKa) were tested for their regenerative capabilities when added to phenol/water (90/10). Results are summarized in Table IV. All of the acids studied appeared to have some beneficial effect. The data indicates that the acid effectiveness parallels the pKa values. Of all the acids, the sulfonic acids appear to be the most useful. This is probably due, at least in part, to the fact that these acids are soluble in the phenol/H$_2$O system. In contrast, the strong mineral acids are insoluble (HCl, H$_2$SO$_4$). In addition, the sulfonic acids, being a model of the ion exchange resin studied, may possess similar attractions towards the liberated tars.

In addition, the effectiveness of paratoluenesulfonic acid in other solvent systems was tested. The results are displayed in Table V.

TABLE IV
VARIOUS ACIDS USED IN REGENERATION[1]

| Run No. | Acid | pKa | Acidity, meq./gm. | % Conversion | Comment |
|---|---|---|---|---|---|
| 1 | p-toluenesulfonic | 1 | 4.28 | 68 | |
| 2 | benzenesulfonic | 1 | 4.28 | 67 | |
| 3 | Conc. H$_2$SO$_4$ | 1.92 | 4.10 | 70 | Immiscible |
| 4 | Conc. HCl | 1 | 3.97 | 61 | Immiscible |
| 5 | Acetic | 4.75 | 3.67 | 25 | |
| 6 | Trifluoroacetic | 1 | 4.08 | 55 | |
| 7 | Citric | 3.08[2] | 4.01 | 39 | |
| 8 | Chloroacetic | 2.85 | 3.96 | 36 | |
| 9 | (Phenol/H$_2$O only) | 9.89 | 3.60 | 17 | |

[1]Regeneration involved washing 35 grams of resin in a small diameter column with phenol/H$_2$O (90/10) containing 0.0176 mole of acid. PKa values are from Handbook of Chemistry and Physics. % Conversion represents a 15 minute bisphenol-A batch reaction. The resin used was described above as sample No. 3 in Table II.
[2]First ionization constant.

TABLE V
REGENERATION EXPERIMENTS USING VARIOUS SOLVENTS

| Run No. | Solvent System | Acidity, meq./gm. | % Conversion |
|---|---|---|---|
| 1. | phenol/H$_2$O | 4.28 | 68 |
| 2. | CH$_3$OH/H$_2$O | 3.62 | 12 |
| 3. | acetone/H$_2$O | 3.60 | 18 |
| 4. | acetic acid/H$_2$O | 3.84 | 23 |
| 5. | dioxane/H$_2$O | 3.69 | 14 |

Inactive resin (35 grams) was washed with 3.35 grams PTSA dissolved in 200 milliliters of solvent (10% water). % conversion represents 15 minute bisphenol-A batch reaction. The resin was described as Sample No. 3 in Table II.

EXAMPLE 6

Regeneration of Ion-Exchange Resin A Used As Catalyst in the "Bisphenol-C" Reaction Virgin Ion Exchange Resin A (11 grams, dry weight) was charged to a small continuous reactor, and the rate of formation of bisphenol-C [bis-1,1,-(4-hydroxyphenyl)cyclohexane; the reaction product of phenol and cyclohexanone] was measured by determining the percent water generated by Karl Fischer analysis. The initial reaction rate was $5.9 \times 10^{-5}$ mole/minute/gram of resin. After 12 hours of continuous operation, the reaction rate had dropped to $1.1 \times 10^{-5}$ mole/minute/gram of resin. Regeneration of the resin was then carried out directly in the reactor by using the PTSA method. A mixture of 180 milliliters of phenol, 20 milliliters of water, and 3.35 grams of p-toluenesulfonic acid monohydrate was passed through the resin catalyst bed. After regeneration, the bisphenol-C reaction rate was $6.0 \times 10^{-5}$ mole/minute/gram resin.

EXAMPLE 7

By procedures analogous to that described in Example 6, the reaction rate of Ion Exchange Resin B and Ion Exchange Resin C in the bisphenol-C reaction were determined. The results are shown below in Table VI:

TABLE VI

| Ion Exchange Resin | Reaction Rate X 10⁵ | | |
|---|---|---|---|
| | Initial | After Operation | After PTSA Regeneration |
| B | 7.0 | 2.4 (6 hours) | 4.1 |
| C | 8.86 | 2.94 (14 hours) | 8.80 |

As the foregoing Examples illustrate, the regeneration of acidic cation exchange resin by the process of the invention is evidenced by a significant increase in the acidity of the resin and/or by a significant increase in catalytic activity in a model reaction.

What is claimed is:

1. Process for regenerating sulfonated acidic cation exchange resin that has been deactivated with phenol-derived organic tars or by contamination with metallic ions, or both, which process comprises passing a phenol-water mixture containing an acid having a pKa of less than about 3 through said resin, wherein the major component of said mixture is phenol.

2. The process of claim 1 wherein the acid has a pKa of less than about 2.

3. The process of claim 1 wherein the acid is an organic acid.

4. The process of claim 1 wherein the acid is a sulfonic acid.

5. The process of claim 4 wherein the sulfonic acid is benzenesulfonic acid or para-toluenesulfonic acid.

6. The process of claim 1 wherein the resin is fouled with organic tars derived from a bisphenol-A process.

7. The process of claim 1 wherein the resin is a macroreticular resin comprising the sulfonated product of a styrene/divinylbenzene copolymer.

8. The process of claim 1 wherein the resin is fouled with organic tars derived from a phenol/carbonyl compound condensation process.

* * * * *

UNITED STATES PATENT AND TRADEMARK OFFICE
CERTIFICATE OF CORRECTION

PATENT NO. : 4,051,079

DATED : September 27, 1977

INVENTOR(S) : Earl George Melby

It is certified that error appears in the above-identified patent and that said Letters Patent are hereby corrected as shown below:

Column 4, line 23, before "G. Zundel" insert -- * --

Columns 5-6, TABLE III, column headed "Conversion" should be changed to read % Conversion --

Columns 7-8, TABLE III-continued, column headed "Conversion" should be changed to read -- % Conversion --

Signed and Sealed this

Tenth Day of July 1979

[SEAL]

Attest:

*Attesting Officer*

LUTRELLE F. PARKER
*Acting Commissioner of Patents and Trademarks*